United States Patent

Hoshowski et al.

[11] Patent Number: 4,678,475
[45] Date of Patent: Jul. 7, 1987

[54] DYE-CONDITIONER COMPOSITION THAT IS NON-STAINING TO SKIN CONTAINING A CERTIFIED VIOLET DYE AND A QUATERNARY AMMONIUM COMPOUND

[75] Inventors: Myra A. Hoshowski, Addison; Chaitanya Patel, Hanover Park, both of Ill.

[73] Assignee: Helene Curtis, Inc., Chicago, Ill.

[21] Appl. No.: 820,124

[22] Filed: Jan. 21, 1986

[51] Int. Cl.$^4$ .............. A61K 7/13; D06P 1/642; D06P 3/14
[52] U.S. Cl. .............. 8/606; 8/405; 8/917; 424/70
[58] Field of Search .............. 8/426, 428, 524, 527, 8/528, 606, 405, 917; 424/70

[56] References Cited

U.S. PATENT DOCUMENTS 4,453,943  6/1984  Balliello .............. 8/917
4,472,297  9/1984  Bolich, Jr. et al. .............. 252/531

FOREIGN PATENT DOCUMENTS 0152194  8/1985  European Pat. Off.
0155806  9/1985  European Pat. Off.

OTHER PUBLICATIONS

*Cosmetics Science and Technology,* Balsam et al, 1975, pp. 92-95, 292-293, 345-361.

Silver Fox Conditioner, ingredients list, Manufactured by Morning Side Laboratories.

*Primary Examiner*—Paul Lieberman
*Assistant Examiner*—L. Skaling
*Attorney, Agent, or Firm*—Mason, Kolehmainen, Rathburn & Wyss

[57] ABSTRACT

A dialkyl quaternary ammonium compound falling within the formula

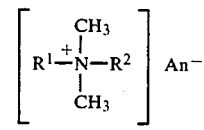

wherein $R^1$ and $R^2$ are the same or different straight chain alkyl radicals $C_nH_{2n+1}$ wherein n is predominantly at least 12, and particularly where n equals predominantly 12-16, unexpectedly prevents Ext. D & C Violet No. 2 dye from staining skin while providing better deposition of the Ext. D & C Violet No. 2 onto human hair and wool to decrease or eliminate hair and wool yellowing. These fatty radicals $R^1$ and $R^2$ are generally derived from coconut oil, lauric acid, myristic acid, or palmitic acid and $An^-$ is any anion, particularly the halogen ions and particularly the chloride ion.

20 Claims, No Drawings

DYE-CONDITIONER COMPOSITION THAT IS NON-STAINING TO SKIN CONTAINING A CERTIFIED VIOLET DYE AND A QUATERNARY AMMONIUM COMPOUND

FIELD OF THE INVENTION

The present invention is directed to a dye composition achieving new and unexpected deposition of External D & C Violet No. 2 dye onto human hair without skin staining. More particularly, the present invention is directed to a Ext. D & C Violet No. 2 dye-containing composition containing a long chain dialkyl quaternary ammonium salt having two long chain (predominantly $C_{12}$–$C_{16}$) alkyl radicals such as the fatty long chain alkyl radicals derived from coconut oil, lauric acid, myristic acid or palmitic acid. It has been found that these di-fatty quaternary ammonium salts, such as the di-fatty quaternary ammonium chlorides, provide tinctorially effective increased deposition of Ext. D & C Violet No. 2 dye onto human hair to reduce hair yellowing while unexpectedly preventing the dye from staining the scalp.

BACKGROUND OF THE INVENTION AND PRIOR ART

Gray and white hair yellows naturally with age or with the use of yellow-colored shampoos, hair sprays and the like. Accordingly, the art recognizes that Ext. D & C Violet No. 2 can be used in shampoos, rinses, conditioners and the like to neutralize this yellow cast on gray and white hair by replacing the yellow color with small, tinctorially effective amounts of Ext. D & C Violet No. 2 to permit the hair to return to its natural color. One such product is Clairol's Shimmer Lights shampoo containing water, sodium lauryl sulfate, lauramide DEA, amodimethicone, hydrolyzed animal protein, lauryl alcohol, tallowtrimoniumchloride, glycol stearate, citric acid, fragrance, monoxynol-10, methyl and propyl parabens, imidazolidinyl urea, disodium EDTA, External D & C Violet No. 2, D & C Violet No. 2, and other ingredients at a pH of 6.08. Another example of a similar commercially available Ext. D & C Violet No. 2 containing conditioner is Silver Fox shampoo for gray hair manufactured by Morningside Laboratories. This product includes water, ammonium lauryl sulfate, lauramide DEA, glycol stearate, hydrolyzed animal protein, tetrasodium EDTA, hydroxypropyl methylcelulose, imidazolidinyl urea, methyl paraben, propylparaben, fragrance, and Ext. D & C Violet No. 2. One of the problems with these and other commercial compositions for removing the yellow cast on gray or white hair by substituting Ext. D & C Violet No. 2 for the yellow cast is that the Ext. D & C Violet No. 2 dye does not have much affinity for human hair and much of the dye from the compositions is wasted after scalp contact and rinsing. Because much of the Ext. D & C Violet No. 2 dye is never attached to the hair, much of it flows over the scalp of the user where the dye has a greater affinity for the scale than for the hair resulting in scalp staining. That portion of the Ext. D & C Violet No. 2 that does remain with the hair is loosely bound and easily washes away from the hair within one or two washings.

Consequently, no existing product provides a composition capable of tinctorially effective Ext. D & C Violet No. 2 color change on gray or white hair without simultaneous skin or scalp staining. In accordance with the present invention, it has been found that dialkyl quaternary ammonium compounds having two alkyl radicals predominantly in the $C_{12}$ to $C_{18}$ range dramatically and unexpectedly provide tinctorially effective deposition of External D & C Violet No. 2 dye onto human hair to reduce or eliminate yellowing of hair without the prior art problem of skin or scalp staining.

Long chain monoalkyl quaternary ammonium compounds and hydrogenated tallow-derived quaternary salts have been used in cream rinse products as hair detangling agents where the long alkyl chains are derived from coconut oil or tallow fat (predominantly $C_{12}$ to $C_{18}$). The monoalkyl quaternary ammonium surfactants penetrate into wet hair, and interact with hair structural bonds to relax the wet hair fiber while, at the same time, providing a lubricating film to the hair surface that contributes to the ease of wet combing—see An Introduction to Quaternary Ammonium Compounds, Cosmetics & Toiletries, Vol. 94, Nov. 1979, pp. 33–41. The long chain monoalkyl quaternary ammonium compounds also are known in cream rinses and the like to have an effect of binding fatty alcohols and esters, perfume oils and other waxy and oily constituents to the hair surface and to improve the hair texture by softening it and eliminating static flyaway.

One of the common mono fatty alkyl quaternary ammonium compounds used in hair conditioning products is cetyl trimethyl ammonium chloride (CETAC) having a Cosmetic, Toiletry and Fragrance Association (CTFA) name cetrimonium chloride. Another long chain alkyl quaternary ammonium compound commonly used in hair conditioning products is stearyl dimethyl benzyl ammonium chloride (SDBAC), CTFA name stearalkonium chloride. These long chain monoalkyl quaternary ammonium compounds are used in hair conditioning products at concentrations ranging from tenths of a percent to two percent by weight, since higher concentrations of these materials can produce a higher risk of ocular damage and skin irritation.

In accordance with the present invention, it has been found that particular fatty dialkyl quaternary ammonium compounds in an amount of 0.5 to 2.5 weight percent of a composition containing Ext. D & C Violet No. 2 dye unexpectedly provide a composition capable of substantially reducing or eliminating yellowing of human hair and wool without visible skin staining.

SUMMARY OF THE INVENTION

In brief, it has been found that a dialkyl quaternary ammonium compound falling within the formula

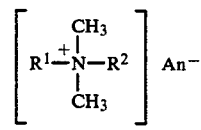

wherein $R^1$ and $R^2$ are the same or different straight chain alkyl radicals $C_nH_{2n+1}$ wherein n is predominantly at least 12, and particularly where n equals predominantly 12–16, unexpectedly prevents Ext. D & C Violet No. 2 dye from staining skin while providing better deposition of the Ext. D & C Violet No. 2 onto human hair and wool to decrease or eliminate hair and wool yellowing. These fatty radicals $R^1$ and $R^2$ are generally derived from coconut oil, lauric acid, myristic acid, or palmitic acid and $An^-$ is any anion, particularly the halogen ions and particularly the chloride ion.

The composition of the present invention generally includes an Ext. D & C Violet No. 2 dye in an amount of 0.001 to 1.0%; one or more of the above-defined di-fatty quaternary ammonium salts 0.5 to 2.5%; water; and optionally, thickening agents, e.g., hydroxyethyl cellulose 0 to 1%; preservatives 0 to 1%; emollients 0 to 3%; one or more fatty alcohols 0 to 2%; and one or more fatty amido amines 0 to 2%, where percentages are by weight based on the total weight of the composition.

The optional fatty alcohol in the composition is one having the formula: $CH_3(CH_2)_nCH_2OH$ wherein n is predominantly at least 12, and particularly predominantly 12 to 16, such as cetyl, myristyl and stearyl alcohols. The fatty alcohols useful in the compositions of the present invention are any that are predominantly solid at room temperature to provide the composition with increased emulsion thickening. The fatty alcohol is added in an amount of about 0.1 to 2 percent by weight of the composition, preferably about 1.0 percent to provide a good appearance to the composition.

The optional fatty ester or fatty amido amine, if included, is particularly one resulting from the reaction of isopropyl alcohol and myristic acid, palmitic acid or mixtures thereof such as that falling within the following formula:

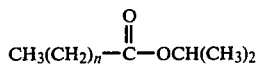

wherein n is predominantly at least 10, and particularly where n is predominantly 10 to 14; or mixtures; and/or a fatty amido amine falling within the formula:

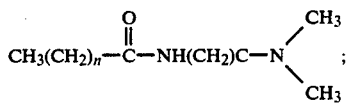

wherein n is predominantly at least 10, and particularly where n is predominantly 10 to 14; or mixtures. The fatty ester or fatty amidoamine is added in amounts of about 0.1 to 2 percent by weight of the composition. It has been found that maximum deposition of Ext. D & C Violet No. 2 is achieved with about 1.0% by weight of the fatty ester, with less deposition at both 2% and 0%, and maximum deposition is achieved at a 0.5 weight percent concentration of the fatty amido amine, with less deposition at 1%.

DETAILED DESCRIPTION OF THE PREFERRED EMBODIMENT

The dye-conditioning composition of the present invention includes a di-fatty quaternary ammonium compound falling within the formula

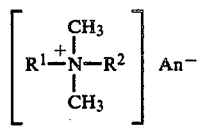

wherein $R^1$ and $R^2$ are the same or different straight chain alkyl radicals $C_nH_{2n+1}$ wherein n is predominantly at least 12, and particularly where n is predominantly 12 to 16; and $An^-$ is any anion. These di-fatty quaternary ammonium salts achieve tinctorially effective, more dramatic and unexpected deposition of a Violet dye falling within the structural formula:

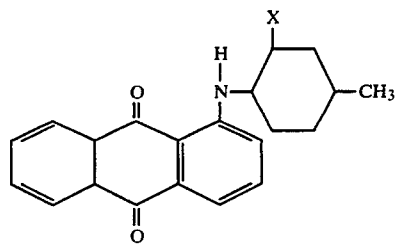

without skin staining, wherein X is H or $SO_3M$ and wherein M is any alkali metal, amine, or substituted amine. The composition of the present invention is particularly useful for deposition of External D & C Violet No. 2 dye, wherein M is sodium.

In accordance with an important feature of the present invention, the di-fatty quaternary ammonium compounds included in the composition of the present invention permit dramatic and unexpected deposition of the above-defined Violet dyes onto human hair and wool without skin or scalp staining. Without being limited to any particular theory, it is theorized that the particular above-defined di-fatty quaternary ammonium salts form a complex with the above-defined Violet dyes and the formed complex has increased affinity for the hair and substantially decreased affinity for skin.

Examples of suitable dialkyl fatty quaternary ammonium compounds providing new and unexpected deposition of External D & C Violet No. 2 dye without skin staining are dicetyl dimethyl ammonium chloride having a CTFA name dicetyldimoniumchloride as follows:

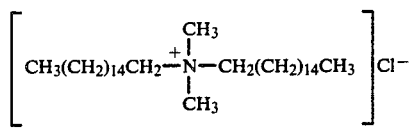

and dilauryl dimethyl ammonium chloride having a CTFA name dilauricdimonium chloride:

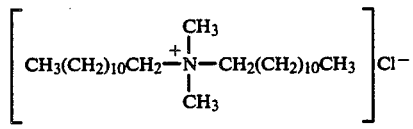

It should be noted that the fatty alkyl radicals are predominantly $C_{12}$ to $C_{16}$ but, as well known, these fatty radicals include a substantial percentage of shorter and longer alkyl radicals. The fatty radicals $R^1$ and $R^2$ cannot be an alkyl having predominantly a 10 carbon chain length since this quaternary ammonium compound causes significant eye irritation or ocular damage. Further, it should be noted that the distearyl dimethyl ammonium chloride, CTFA name distearyldimonium chloride:

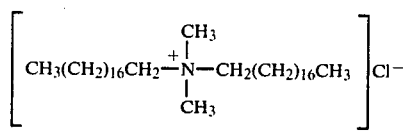

has no effect upon deposition of External D & C Violet No. 2 dye upon human hair or wool.

The Violet dye can be included in an amount of 0.001% to 1.0% by weight of the composition, but to achieve the full advantage of the present invention, the Violet dye should be included in the composition in an amount less than about 0.1% by weight of the composition and particularly at a concentration of 0.01 to 0.05% by weight of the composition. Excellent deposition of the violet dyes onto human hair without concomitant skin or scalp staining is achieved within this range of concentration for the Violet dye. The di-fatty quaternary ammonium compound interacts with the Violet dyes falling within the above structural formula to achieve increased deposition of these dyes onto human hair and wool unexpectedly without skin staining. The di-fatty quaternary ammonium compounds of the present invention should be included in the composition in an amount of at least 0.5% by weight of the composition, with particularly new and unexpected results achieved within the range of 1.5-2.5% by weight of the composition.

The compositions can be thickened with, for example, cellulose derivatives such as methylcellulose, hydroxyethylcellulose, hydroxypropylmethylcellulose and carboxymethylcellulose, sodium alginate, gum arabic, and various polymeric thickeners, such as acrylic acid derivatives. It is also possible to use inorganic thickeners such as bentonite. These thickeners are preferably present in an amount from 0.5 to 10% by weight and in particular from 0.5 to 3% by weight, based on the total weight of the composition.

Other common additives may be incorporated into the composition as long as the basic properties of the hair dye-conditioner are not adversely affected. These additives include, but are not limited to, commonly used fragrances, opacifiers, pearlescing agents, preservatives, sequestering agents, and the like, and will usually be present in weight percentages of less than 1% each, and 2% to 5% in total. The cosmetic vehicle is generally water but it is also possible to add organic solvents to the compositions in order to solubilize compounds which would not be sufficiently soluble in water. Suitable solvents include lower alkanols such as ethanol and isopropanol; polyols such as glycerol, glycols or glycol ethers, such as 2-butoxyethanol, ethylene glycol, ethylene glycol monoethyl ether, propylene glycol and diethylene glycol monoethyl ether monomethyl ether, and mixtures thereof. These solvents may be present in the dye-conditioner composition of the present invention in an amount from 1 to 75% by weight and in particular from 5 to 50% by weight, relative to the total weight of the composition.

Generally, to achieve the full advantage of the present invention, the composition is as follows:

| Components | wt % |
| --- | --- |
| Water, soft | q.s. to 100 |
| Thickener, e.g., Hydroxyethyl cellulose | 0 to 0.5 |
| Fatty alcohol | 0 to 1.0 |

-continued

| Components | wt % |
| --- | --- |
| Di-fatty quaternary ammonium, e.g., chloride | 0.5 to 2.5 |
| Fatty amido amine | 0 to 1.0 |
| Emollient | 0 to 3.0 |
| Ext. D & C Violet No. 2 | 0.01 to 0.05 |
| Preservative, e.g., Kathon CG (methylchloroisothiazolinone and methylisothiazolinone) | 0.05 |

The composition is formulated by adding the thickeners, e.g., hydroxyethyl cellulose (if used) to soft water, agitating for about twenty minutes, and thereafter heating the hydroxyethyl cellulose-water composition to approximately 160° F. An additional quantity of soft water then is heated to about 160° F. to which the di-fatty quaternary ammonium compound is added as well as any fatty alcohol, fatty ester and fatty amido amine, if used. The two heated soft water compositions then are mixed together and cooled to approximately 110° F. prior to the addition of the Violet dye, emollient and preservative.

The compositions of the present invention preferably include an emollient such as a glycol; glycol ether; glyceride; polyglyceride; fatty acid; salt of a fatty acid, such as isopropyl myristate and isopropyl palmitate; or mixtures in an amount of about 1.0 to 3.0 percent by weight of the composition to improve the lubrication and luster of the hair. Suitable emollients include isopropyl myristate (IPM); isopropyl palmitate (IPP); polypropylene glycol ether of cetyl alcohol (PPG-30 Cetyl Ether); propylene glycol; hexylene glycol; hydroxylated or acetylated lanolin or a lanolin ester; fatty alcohol; a wax; fatty acid ester; partially sulphated fatty alcohol, such as lanette wax; lecithin, aliphatic alcohol, natural triglyceride; polyolester; or an oil such as petrolatum, almond, avocado, pear, mink, castor, mineral and wheat germ. The emollients contribute to luster, wet and dry comb, reduced flyaway, and/or feel and the like.

To show that the composition of the present invention is useful without the additional non-essential emollients, fatty alcohols, fatty esters, fatty amido amines, and the like additives and to show that the mono fatty alkyl ammonium chlorides and the distearyldimonium chlorides are ineffective, bleached blonde hair was treated using simple solutions of water, di-fatty quaternary ammonium chloride at 2.1% active, and Ext. D and C Violet No. 2 at 0.02%, adjusted to pH 6.0. A summary table of results follows:

| Fatty Quaternary Ammonium Compound | Deposition 0 = None, 5 = Most |
| --- | --- |
| Dicetyldimmonium chloride | 4.5 |
| Dicocodimmonium chloride | 3.0 |
| Distearyldimmonium chloride | 0 |
| Steartrimonium chloride | 0 |
| Cetrimonium chloride | 0 |

In accordance with the preferred embodiment, compositions were fomulated including stearyl alcohol, dicetyldimmonium chloride, and stearamidopropyl dimethylamine for deposition of 0.02% External D & C Violet No. 2 onto standard virgin white human hair tresses, all one lot from DeMeo Brothers, New York. Each tress weighed 1 gram. The tresses were bleached with a salon persulfate bleaching treatment (Frosting Plus from Helene Curtis) for 45 minutes. Unbleached tresses give similar results as bleached tresses but with much less deposition which is difficult to read accurately. Therefore, the results are all given for bleached hair.

Each tress was treated with 1 gram of test conditioner. The conditioner was left on for 2 minutes and rinsed under 100° F. tap water for 30 seconds. The tress was blotted dry, combed through and allowed to air dry. The tress was examined visually for reduction of yellowing versus an untreated control and for any deposition of Violet color versus an untreated control. The results were obtained visually since there is no existing light reflectance apparatus sensitive enough to determine, accurately, deposition of Violet dyes onto either human hair or wool at the levels of deposition of Violet dyes in reducing yellowing in accordance with the present invention. The Violet dyes, in small but tinctorially effective amounts, as used to reduce or eliminate yellowing in accordance with the present invention, are more accurately determined visually using the observations of a plurality of observances, as accomplished for the data of Tables 1–4. The compositions of the present invention were applied to human hair rather than wool since for the thickened emulsions used in the testing, the compositions can be combed through hair swatches uniformly and evenly which would not be possible if woven wool were used. Thinner compositions could not be used for testing on wool since the composition itself would not have been sufficiently homogenous for accurate results. The results were tabulated in the following Tables 1–4:

TABLE 1

0.02% Ext. D & C Violet No. 2
1.0% Stearyl Alcohol
ADOGEN 432 ET - Dicetyldimonium Chloride
LEXAMINE S-13 - Stearamidopropyl Dimethylamine

| % ADOGEN 432 ET | % LEXA-MINE S-13 | Emollient | % Emollient | 0 = None 5 = Most Deposition |
|---|---|---|---|---|
| 0 | 0 | — | 0 | 0 |
| 2.1 | 0 | — | 0 | 2 |
| 2.1 | 0.5 | — | 0 | 4 |
| 2.1 | 0.5 | Caprylic/capric triglyceride | 1.0 | 4 |
| 2.1 | 0.5 | Caprylic/capric triglyceride | 2.0 | 4 |
| 2.1 | 0.5 | Caprylic/capric triglyceride | 3.0 | 2 |
| 2.1 | 0.5 | PPG-30 Cetyl Ether | 1.0 | 2 |
| 2.1 | 0.5 | Propylene Glycol | 1.0 | 2 |
| 2.1 | 0.5 | Hexylene Glycol | 1.0 | 2 |
| 2.1 | 0.5 | IPM | 1.0 | 5 |
| 2.1 | 0.5 | IPM | 2.0 | 3 |
| 2.1 | 0.5 | IPP | 1.0 | 2 |

As shown in Table 1, the External D & C Violet No. 2 did not deposit at all without the addition of the quaternary ammonium compound. Also shown in Table 1, with the addition of 2.1% dicetyldimonium chloride alone, without any amine or emollient, the External D & C Violet No. 2 deposited to a unit value of 2 where 0 is no deposition and 5 is the most deposition found in the formulations tested.

As shown in the following Table 2, Ext. D & C Violet No. 2 could not be deposited at all with the same 0.02% concentration or with an increased concentration of 0.05% of External D & C Violet No. 2 in a composition containing distearyl dimonium chloride with or without an emollient and/or a fatty amido amine:

TABLE 2

0.02% Ext. D & C Violet No. 2
1.0% Stearyl Alcohol
AROSURF TA-100 - Distearyldimonium Chloride
LEXAMINE S-13 - Stearamidopropyl Dimethylamine

| % ARO-SURF TA-100 | % LEXA-MINE S-13 | Emollient | % Emollient | 0=None 5=Most Deposition |
|---|---|---|---|---|
| 2.1 | 0 | — | 0 | 0 |
| 2.1 | 0.5 | — | 0 | 0 |
| 2.1 | 1.0 | — | 0 | 0 |
| 2.1 | 0.5 | Caprylic/capric triglyceride | 2.0 | 0 |

Increased level of Ext. D & C Violet No. 2 to 0.05%

| % ARO-TA-100 | % LEXA-MINE S-13 | Emollient | % Emollient | % Deposition |
|---|---|---|---|---|
| 2.1 | 1.0 | — | 0 | 0 |
| 2.1 | 0 | Caprylic/capric triglyceride | 2 | 0 |

As shown in Table 3, results similar to those obtained in Table 1 were achieved using a dilauryldimonium chloride instead of the dicetyldimonium chloride of Table 1, with and without a fatty amido amine (stearamidopropyl dimethylamine) and/or emollient.

TABLE 3

| % Ext. D & C Violet No. 2 | % AD-OGEN 462 | % LEXA-MINE S-13 | Emollient | % Emollient | 0=None 5=Most Deposition |
|---|---|---|---|---|---|
| 0.01 | 2.1 | 0 | — | 0 | 3 |
| 0.01 | 2.1 | 1.0 | — | 0 | 3 |
| 0.01 | 2.1 | 1.0 | Caprylic/capric triglyceride | 3.0 | 1 |
| 0.02 | 2.1 | 0 | — | 0 | 3 |
| 0.02 | 2.1 | 0 | Caprylic/capric triglyceride | 2.0 | 2 |
| 0.02 | 2.1 | 0 | Caprylic/capric triglyceride | 2.0 | 2 |
| 0.05 | 2.1 | 0.5 | Caprylic/capric triglyceride | 3.0 | 5 |

As shown in the following Table 4, various compositions were prepared, as described above, and labeled Compositions A through G, each containing 0.02% External D & C Violet No. 2 as well as stearyl alcohol, stearamidopropyl dimethylamine and all but composition D containing 3% by weight dicetyl dimonium chloride. Every composition except D included an emollient to determine the effect of various emollients upon the compositions of the present invention. It was concluded from Tables 1 and 3 that the presence or selection of emollient is not critical to the practice of the invention. The results are shown in Table 4:

TABLE 4

| Ingredient | A wt % | B wt % | C wt % | D wt % | E wt % | F wt % | G wt % |
|---|---|---|---|---|---|---|---|
| Water, soft | 42.0 | 42.0 | 42.0 | 44.0 | 42.0 | 41.5 | 42.0 |
| hydroxyethyl cellulose | 0.5 | 0.5 | 0.5 | 0.5 | 0.5 | 0.5 | 0.5 |
| water, soft | 42.0 | 42.0 | 42.0 | 44.0 | 42.0 | 41.5 | 43.0 |
| Stearyl Alcohol | 1.0 | 1.0 | 1.0 | 1.0 | 1.0 | 1.0 | 1.0 |
| Dicetyl dimonium chloride | 3.0 | 3.0 | 3.0 | — | 3.0 | 3.0 | 3.0 |
| Ext. D & C | 0.02 | 0.02 | 0.02 | 0.02 | 0.02 | 0.02 | 0.02 |

TABLE 4-continued

| Ingredient | A wt % | B wt % | C wt % | D wt % | E wt % | F wt % | G wt % |
|---|---|---|---|---|---|---|---|
| Violet No. 2 | | | | | | | |
| Stearamidopropyl dimethylamine | 0.5 | 0.5 | 0.5 | 0.5 | 0.5 | 0.5 | 0.5 |
| PPG 30 Cetyl Ester | 1.0 | — | — | — | — | — | — |
| Propylene glycol | — | 1.0 | — | — | — | — | — |
| Silute L-720 | — | — | — | — | — | — | — |
| Hexylene glycol | — | — | 1.0 | — | — | — | — |
| Isopropyl Myristate | — | — | — | — | 1.0 | 2.0 | — |
| Isopropyl Palmitate | — | — | — | — | — | — | 1.0 |
| pH | 5.50 | 5.62 | 5.96 | 5.69 | 5.48 | 5.62 | 5.50 |
| Deposition | 2 | 2 | 2 | 0 | 5 | 3 | 2 |

0 = None
5 = Most

It should be understood that the present disclosure has been made only by way of preferred embodiment and that numerous changes in details of construction, combination and arrangements of parts may be resorted to without departing from the spirit and scope of the invention as herein claimed.

What is claimed and sought to be secured by Letters Patent of the United States is:

1. A hair dye composition comprising a tinctorially effective amount of a Certified Violet dye and a quaternary ammonium compound of the formula:

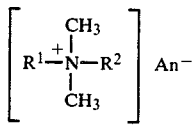

wherein An$^-$ is any anion and R$^1$ and R$^2$ are the same or different straight chain alkyl radicals C$_n$H$_{2n+1}$ wherein n is predominantly 12 to 16, wherein the quaternary ammonium compound is included in the composition in an amount sufficient to prevent the Violet dye from visibly staining skin.

2. The composition of claim 1 wherein the Violet dye is a dye of the formula

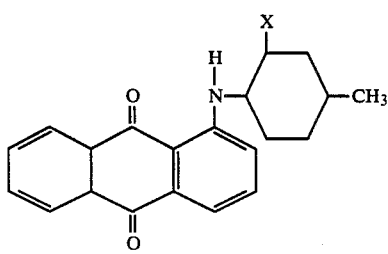

wherein X is H or SO$_3$M and wherein M is any alkali metal, amine or substituted amine.

3. The composition of claim 2 wherein M is sodium.

4. The composition of claim 1 wherein An$^-$ is a halogen ion.

5. The composition of claim 4 wherein An$^-$ comprises Cl$^-$.

6. The composition of claim 1 wherein the quaternary ammonium compound is included in the composition in an amount of at least 0.5% by weight of the composition.

7. The composition of claim 6 wherein the quaternary ammonium compound is included in the composition in an amount of 0.5% to 2.5% by weight of the composition.

8. The composition of claim 1 wherein the violet dye is included in the composition in an amount of 0.001% to 1.0% by weight of the composition.

9. The composition of claim 8, wherein the violet dye is included in the composition in an amount less than 0.1% by weight of the composition.

10. The composition of claim 8 wherein the violet dye is included in the composition in an amount of 0.01 to 0.05% by weight of the composition.

11. The composition of claim 1 further including a fatty ester of the formula

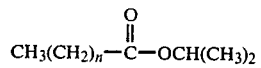

wherein n is at least 10.

12. The composition of claim 11 wherein the n defining the carbon chain length of the fatty ester is predominantly 10 to 14 in an amount of 0.001% to 1.0% by weight of the composition.

13. The composition of claim 1 further including a fatty alcohol predominantly solid at room temperature in an amount of 0.001% to 1.0% by weight of the composition.

14. The composition of claim 13 wherein the fatty alcohol is one having the formula CH$_3$(CH$_2$)$_n$CH$_2$OH wherein n is at least 12.

15. The composition of claim 14 wherein the n defining the carbon chain length of the fatty alcohol is predominantly 12 to 16.

16. The composition of claim 1 further including a fatty amidoamine having the formula:

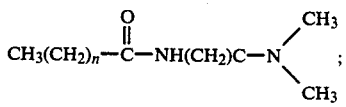

wherein n is predominantly at least 10, in an amount of 0.001% to 1.0% by weight of the composition.

17. The composition of claim 16 wherein the n defining the carbon chain length of the fatty amidoamine is predominantly 10 to 14.

18. The composition of claim 1 further including an emollient in an amount of 0.001% to 3.0% by weight of the composition.

19. The composition of claim 18 wherein the emollient is selected from the group consisting of glycols, glycol ethers, glycerides, polyglycerides, fatty acids, salts of fatty acids and mixtures thereof.

20. A method of reducing yellowing of yellowed human hair with a violet dye-containing composition without substantial visible skin coloration comprising contacting human hair with a composition containing a liquid carrier; a tinctorially effective amount of a violet dye; and a di-fatty quaternary ammonium compound of the formula

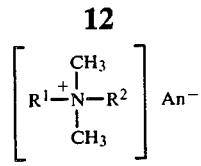

wherein $An^-$ is any anion and $R^1$ and $R^2$ are the same or different straight chain alkyl radicals $C_nH_{2n+1}$ wherein n is at least 12, wherein the quaternary ammonium compound is included in the composition in an amount sufficient to prevent the Violet dye from visibly staining skin.

* * * * *

UNITED STATES PATENT AND TRADEMARK OFFICE
CERTIFICATE OF CORRECTION

PATENT NO. : 4,678,475
DATED : July 7, 1987
INVENTOR(S) : Myra A. Hoshowski et al It is certified that error appears in the above-identified patent and that said Letters Patent is hereby corrected as shown below:

Column 4, line 4, and

Column 9, line 55, after " formula " delete the following structure

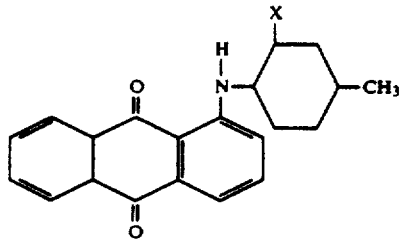

and insert the following correct structure

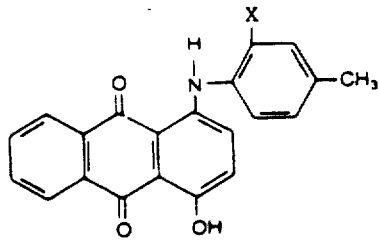

Signed and Sealed this

Seventh Day of August, 1990

*Attest:*

HARRY F. MANBECK, JR.

*Attesting Officer*   *Commissioner of Patents and Trademarks*